US008160201B2

(12) United States Patent
Banchet et al.

(10) Patent No.: US 8,160,201 B2
(45) Date of Patent: Apr. 17, 2012

(54) NON-DESTRUCTIVE CHARACTERIZATION METHOD, ESPECIALLY FOR CHARACTERIZING PARTICLES OF NUCLEAR FUEL FOR A HIGH-TEMPERATURE REACTOR

(75) Inventors: Julien Banchet, Lyons (FR); David Tisseur, Chalon sur Saone (FR)

(73) Assignee: Areva NP, Courbevoie (FR)

( * ) Notice: Subject to any disclaimer, the term of this patent is extended or adjusted under 35 U.S.C. 154(b) by 0 days.

(21) Appl. No.: 12/375,327

(22) PCT Filed: Jul. 18, 2007

(86) PCT No.: PCT/FR2007/001236
§ 371 (c)(1),
(2), (4) Date: Jul. 9, 2009

(87) PCT Pub. No.: WO2008/012417
PCT Pub. Date: Jan. 31, 2008

(65) Prior Publication Data
US 2009/0310745 A1 Dec. 17, 2009

(30) Foreign Application Priority Data

Jul. 28, 2006 (FR) ..................................... 06 06950

(51) Int. Cl.
| | |
|---|---|
| G01N 23/06 | (2006.01) |
| G01N 23/20 | (2006.01) |
| G01N 23/083 | (2006.01) |
| G01N 23/201 | (2006.01) |
| G03H 5/00 | (2006.01) |

(52) U.S. Cl. ................................ 378/53; 378/36; 378/88
(58) Field of Classification Search ..................... 378/36, 378/51, 53, 54, 56, 58, 62, 71, 86–89, 207, 378/210; 250/252.1, 393, 395, 526; 73/865, 73/865.5, 866
See application file for complete search history.

(56) References Cited

U.S. PATENT DOCUMENTS

| | | | | |
|---|---|---|---|---|
| 3,955,086 A | * | 5/1976 | Tsujii et al. | 378/56 |
| 4,262,201 A | * | 4/1981 | Wallisch | 378/54 |
| 4,574,387 A | * | 3/1986 | Gignoux et al. | 378/56 |
| 5,530,732 A | * | 6/1996 | Takemi | 378/73 |
| 6,192,103 B1 | * | 2/2001 | Wormington et al. | 378/73 |
| 6,823,043 B2 | * | 11/2004 | Fewster et al. | 378/86 |
| 7,116,755 B2 | * | 10/2006 | Omote | 378/86 |

FOREIGN PATENT DOCUMENTS

| | | |
|---|---|---|
| EP | 1469302 | 10/2004 |
| WO | WO-02/086421 A | 10/2002 |
| WO | WO-2005/106387 | 11/2005 |

OTHER PUBLICATIONS

Snigirev et al., "On the Possibilities of X-ray Phase Contrast Microimaging by Coherent High-energy Synchotron Radiation", Dec. 1995, American Institute of Physics, Rev. Sci. Instrum. vol. 66 No. 12, pp. 5486-5492.*

Kang et al., "Synchrotron X-Ray Study of Multilayers in Laue Geometry", Proc Spie Int Soc Opt Eng; Proceedings of SPIE—The International Society for Optical Engineeting; X-Ray Sources and Optics 2004, vol. 5537, 2004, pp. 127-132.

Vidal et al., "Investigation of Artefact Sources in Synchrotron Microtomography Via Virtual X-Ray Imaging" Nuclear Instruments & Methods in Physics Research, Section B: Beam Interactions With Materials and Atoms, Elsevier, Amsterdam, NL, vol. 234, No. 3, Jun. 2005, pp. 333-348.

* cited by examiner

*Primary Examiner* — Anastasia Midkiff
(74) *Attorney, Agent, or Firm* — Connolly Bove Lodge & Hutz LLP

(57) ABSTRACT

The aim of the method is to characterize an element (21) comprising a plurality of superposed layers separated from one another by interfaces. It comprises at least the following steps: The element (21) is illuminated with radiation (15) emitted by a source (13); radiation (23) transmitted through the element (21) is collected on a detector (17), this transmitted radiation forming an experimental image of the element (21) on the detector (17), the detector (17) being placed at such a distance from the element (21) that interference fringes appear on the experimental image at the interfaces between the layers; and an approximate value of at least one physical characteristic of at least one given layer is determined by calculation from the experimental image, the determination step being implemented by minimizing the difference between the experimental image and a simulated image of at least part of the experimental image of the element (21).

10 Claims, 4 Drawing Sheets

NON-DESTRUCTIVE CHARACTERIZATION METHOD, ESPECIALLY FOR CHARACTERIZING PARTICLES OF NUCLEAR FUEL FOR A HIGH-TEMPERATURE REACTOR

CROSS REFERENCE TO RELATED APPLICATIONS

This application is a National Phase filing under 35 U.S.C. §371 of PCT/FR2007/001236 filed Jul. 18, 2007, which claims priority to Patent Application No. FR 0606950, filed in France on Jul. 28, 2006. The entire contents of each of the above-applications are incorporated herein by reference.

FIELD OF THE INVENTION

The invention generally relates to non-destructive characterisation methods, in particular for particles of nuclear fuel for a high-temperature reactor.

More specifically, according to a first aspect, the invention relates to a method for characterisation of an element comprising a plurality of superimposed layers which are separated from each other by means of interfaces.

The particles of nuclear fuel for a high-temperature nuclear reactor are substantially spherical and comprise a fissile core which is coated with layers of dense and porous pyrocarbon and ceramic material such as silicon carbide or zirconium carbide. The determination of the density of each layer composing the fuel particle is a necessary parameter for the qualification of this fuel.

BACKGROUND OF THE INVENTION

The method which is most commonly used for this purpose is a flotation method. A plurality of reference particles are sampled from a batch of particles to be characterised. This particle is cut, and pieces of each layer are separated in order to carry out the density measurements. These pieces are placed successively in a liquid whose density varies greatly in accordance with temperature. The temperature of the liquid is then varied and it is noted at what temperature the pieces drift to the bottom of the liquid. The density of the material constituting the piece corresponds to the density of the liquid at that temperature.

This method has the disadvantage of using toxic liquids. Furthermore, this characterisation method is slow and brings about the destruction of the particles of fuel characterised. Finally, its implementation is found to be extremely complex since the pieces of each layer must be separated and identified one by one.

In this context, the object of the invention is to provide a characterisation method which can be used for particles of nuclear fuel for a high-temperature reactor and which is non-destructive, environmentally-friendly and more rapid to implement.

SUMMARY OF THE INVENTION

To this end, the invention relates to a characterisation method of the above-mentioned type, characterised in that it comprises at least the following steps:
  illuminating the element with radiation emitted from a source;
  acquiring on a detector radiation transmitted through the element, this transmitted radiation forming on the detector an experiment image of the element, the detector being placed at such a distance from the element that interference fringes resulting from the modification of the wave front by the element appear on the experiment image at the interfaces between the layers;
  determining an approximate value of at least one physical characteristic of at least one specific layer by means of calculation from the experiment image, the determination step being carried out by minimising the deviation between the experiment image and a simulated image of at least a portion of the experiment image.

The method may also have one or more of the features below, taken individually or in accordance with any technically possible combination:
  the radiation is emitted by an X-ray source;
  the detector is a charge transfer camera for direct or indirect detection;
  the physical characteristic to be determined is the density;
  the physical characteristic to be determined is the thickness;
  the method comprises a prior step for determining the pulsed response of the detector, carried out by:
  acquiring on the detector an experiment image of a sample element;
  calculating a simulated image of at least a portion of the experiment image of the sample element;
  determining the pulsed response of the detector by minimising the deviation between the simulated image and the experiment image of the sample element; and
  the sample element is placed against the detector, the simulated image being carried out for at least one edge of the sample element.

According to a second aspect, the invention relates to the use of the above method in order to characterise a substantially spherical particle which comprises a plurality of layers which are substantially spherical, substantially concentric and superimposed.

According to specific embodiments, the use of the method may have one or more of the following characteristics:
  the experiment image is substantially circular, the simulated image being a line which extends through a diameter of the experiment image; and
  the particle is a particle of nuclear fuel.

BRIEF DESCRIPTION OF THE DRAWINGS

Other features and advantages of the invention will be appreciated from the description given below, by way of non-limiting example, and with reference to the appended Figures, in which.

DETAILED DESCRIPTION OF THE PREFERRED EMBODIMENTS

Figure 1:
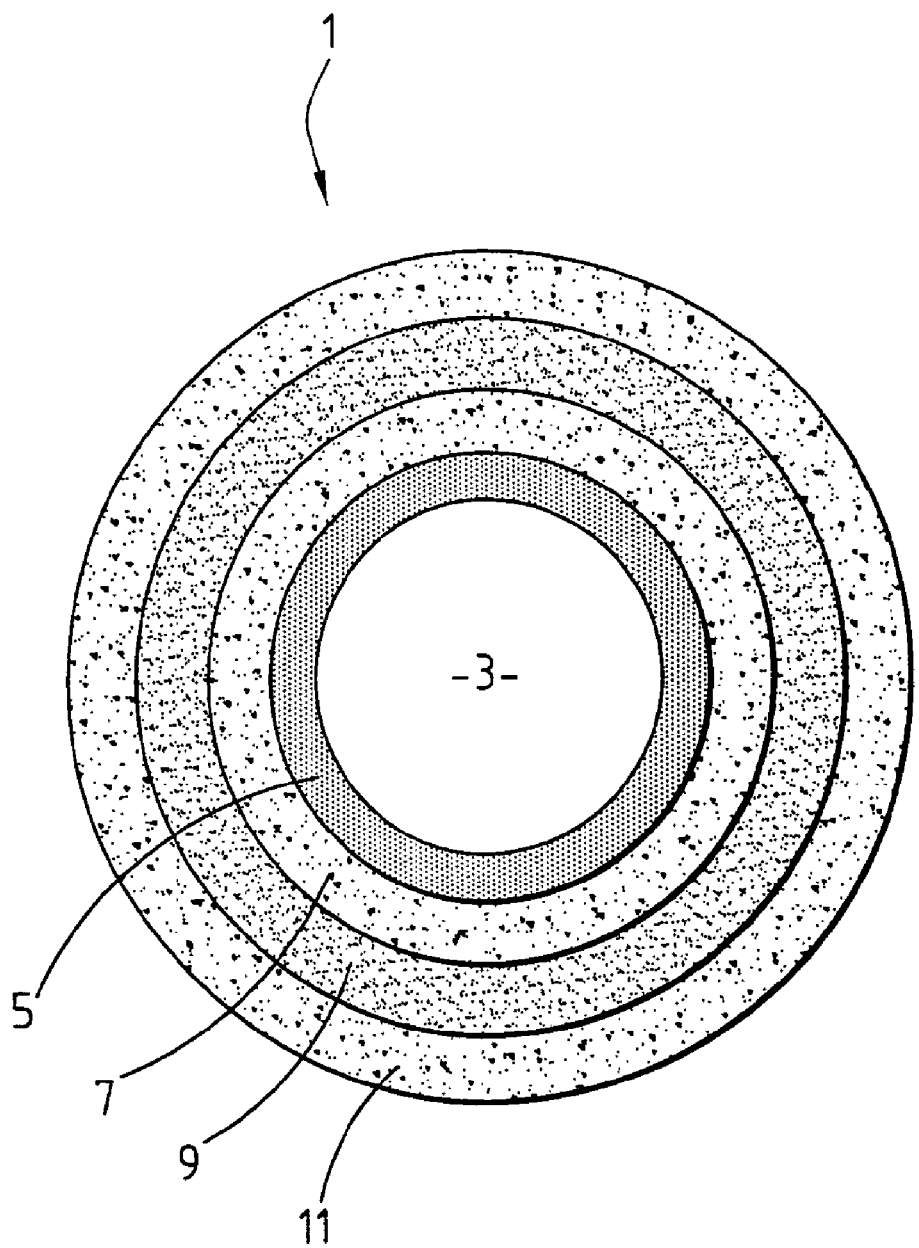
FIG. 1 is a schematic equatorial section illustrating an example of a structure of a particle of nuclear fuel for a high-temperature reactor.

FIG. 1 schematically illustrates a particle 1 of nuclear fuel for a high-temperature or very high-temperature reactor (HTR/VHTR).

In conventional manner, this particle 1 is generally spherical and successively comprises, from the inner side to the outer side:
- a core of fissile material 3, for example, based on $UO_2$ (it may be other types of fissile material, such as UCO, that is to say, a mixture of $UO_2$ and $UC_2$),
- a layer 5 of porous pyrocarbon,
- a first layer 7 of dense pyrocarbon,
- a layer 9 of silicon carbide (or another ceramic such as zirconium carbide), and
- a second layer 11 of dense pyrocarbon.

When such a particle is used, the porous pyrocarbon acts as a reservoir for the fission gases, the silicon carbide acts as a barrier against the diffusion of solid fission products and the dense pyrocarbon provides the mechanical strength of the fission gases under pressure.

The core 3 has, for example, a diameter of approximately 500 μm, it being possible for the diameter to vary from 100 μm to 1000 μm, and the layers 5, 7, 9 and 11 have thicknesses of, for example, 95, 40, 35 and 40 μm, respectively.

It should be noted that the relative dimensions of the core 3 and the layers 5, 7, 9 and 11 have not been complied with in FIG. 1.

The layers, in particular the layers of pyrocarbon 5, 7, 11, are deposited, for example, using a Chemical Vapor Deposition method carried out in an oven with a fluid bed.

Figure 2:
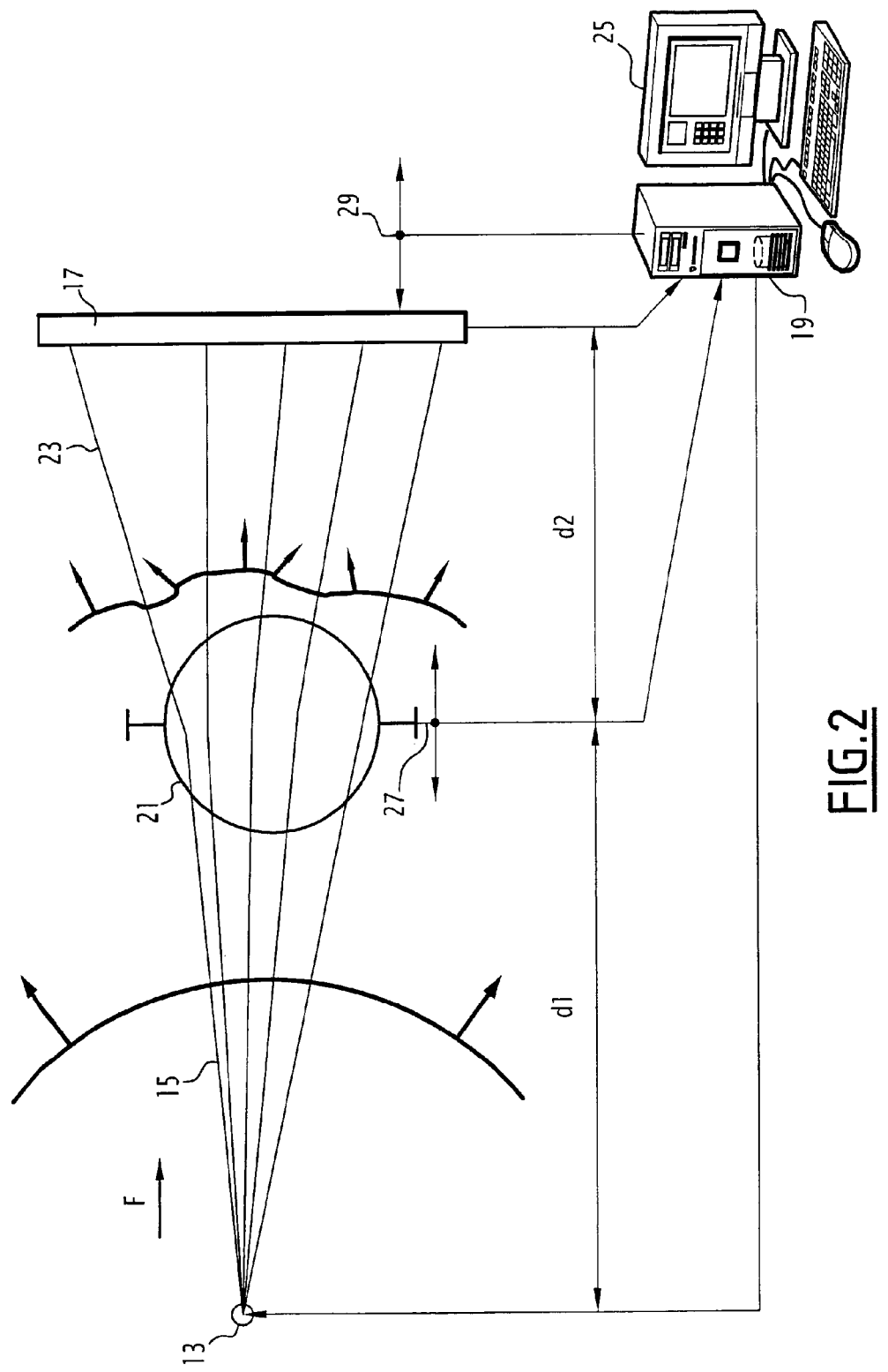
FIG. 2 is a schematic view illustrating an installation for implementing a characterisation method according to the invention.

The installation illustrated in FIG. 2 allows the density and the thickness to be measured for at least the layers 5, 7, 9 and 11.

The installation comprises:
- an X-ray source 13, which is capable of producing X-radiation 15 which forms a beam which extends in a general direction illustrated by the arrow F of FIG. 2;
- a detector 17 which is sensitive to X-radiation and which is positioned so as to intercept the radiation 15 produced by the source 13;
- a data processing unit 19.

The source 13 is preferably an intermittent source which emits monochromatic radiation. The source 13 is, for example, an X-ray tube with micro focus or rotating anode, or a synchotron which may or may not be associated with an optical instrument, for example, a multi-layer mirror or a network of hollow fibres.

A particle 21 to be characterised, of the type described above, is placed at a distance d1 from the source 13, so as to be illuminated by the radiation 15. A fraction 23 of the radiation 15 is transmitted via the particle 21 and strikes the detector 17. This fraction will be referred to as transmitted radiation in the following description. The source 19, the particle 21 and the detector 17 are substantially in alignment.

The detector 17 is, for example, a charge transfer camera, referred to as a CCD camera, with direct detection or indirect detection, that is to say, preceded by a scintillator which allows the camera to be sensitive to the X-radiation transmitted by the source 13. It is placed at a distance d2 from the particle 21 to be characterised. The transmitted radiation 23 forms on the detector 17 an experiment image of the particle 21. It should be noted that the detector can also be a non-digital detector, such as a photostimulable screen, the experiment image being obtained via a supplementary digitisation device.

The experiment image acquired on the detector 17 is typically a two-dimensional image, the various points constituting the experiment image being acquired simultaneously.

As illustrated in FIG. 2, the radiation 15 has, between the source 13 and the particle 21, substantially spherical wave fronts. These fronts become less and less spherical as the distance d1 increases. The X-rays which constitute the transmitted radiation intersect the particle 21 in directions in which this particle has different thicknesses and extend through different materials. Consequently, they will be subject to variable phase shifts, in accordance with the wavelength, the density, the nature and the thickness of the material through which they pass. Consequently, the transmitted radiation 23 has a wave front which is modified by the object. The distance d2 between the detector and the particle 21 is selected so that interference fringes appear on the experiment image of the particle 21 acquired on the detector 17. These interference fringes appear on the experiment image at least at the interfaces between the layers 5, 7, 9 and 11 of the particle owing to the variable phase shift to which the X-rays which pass through the particle 21 are subject.

In this manner, the experiment image is an image which is acquired using the technique known as phase contrast radiography. It corresponds to the superimposition of interference fringes on an image obtained by means of absorption of incident X-rays through the element to be characterised. The image obtained by means of absorption is formed substantially by the radiation transmitted directly through the element to be characterised. Only a small amount of the fraction of the incident radiation which is diffracted or reflected reaches the detector.

The experiment image acquired by the detector 17 is supplied to the data processing unit 19. This comprises, for example, a microcomputer which is provided, inter alia, with display means in the form of a screen 25. The unit 19 is also connected to means 27 which allow the particle 21 to be supported and moved parallel with the radiation 15. The unit 19 is further connected to means 29 which allow the detector 17 to also be moved parallel with the radiation 15.

The method will now be described in detail for allowing the densities and the thicknesses of the layers 5, 7, 9 and 11 of the particle 21 to be determined by means of calculation from the experiment image acquired by the detector 17.

Figure 3:
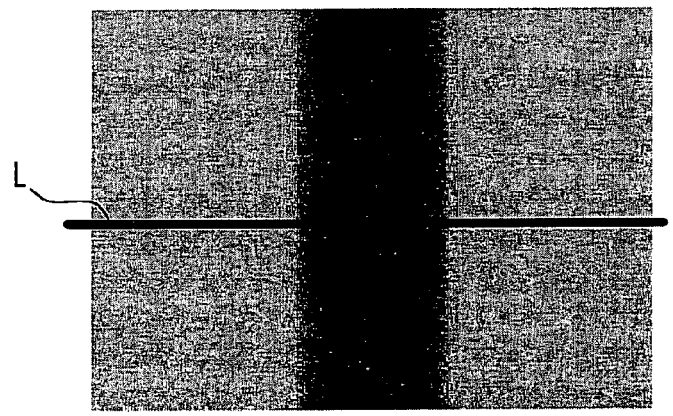
FIG. 3 illustrates the experiment image acquired when the method of the invention is implemented with an element which is constituted by a carbon fibre which comprises a core of silicon carbide.

FIG. 3 illustrates an example of an experiment image which is capable of being acquired by the detector 17. In order to further clarify the description, FIG. 3 illustrates the experiment image of a carbon fibre which comprises a core of silicon carbide which is acquired under the conditions illustrated in FIG. 2. The data-processing means 19 extract a profile of the experiment image, taken in this instance along the line L indicated in FIG. 3. The fibre 31 on the image of FIG. 3 is extended in a vertical direction. The profile L is taken along a horizontal line in FIG. 3.

Figure 4:
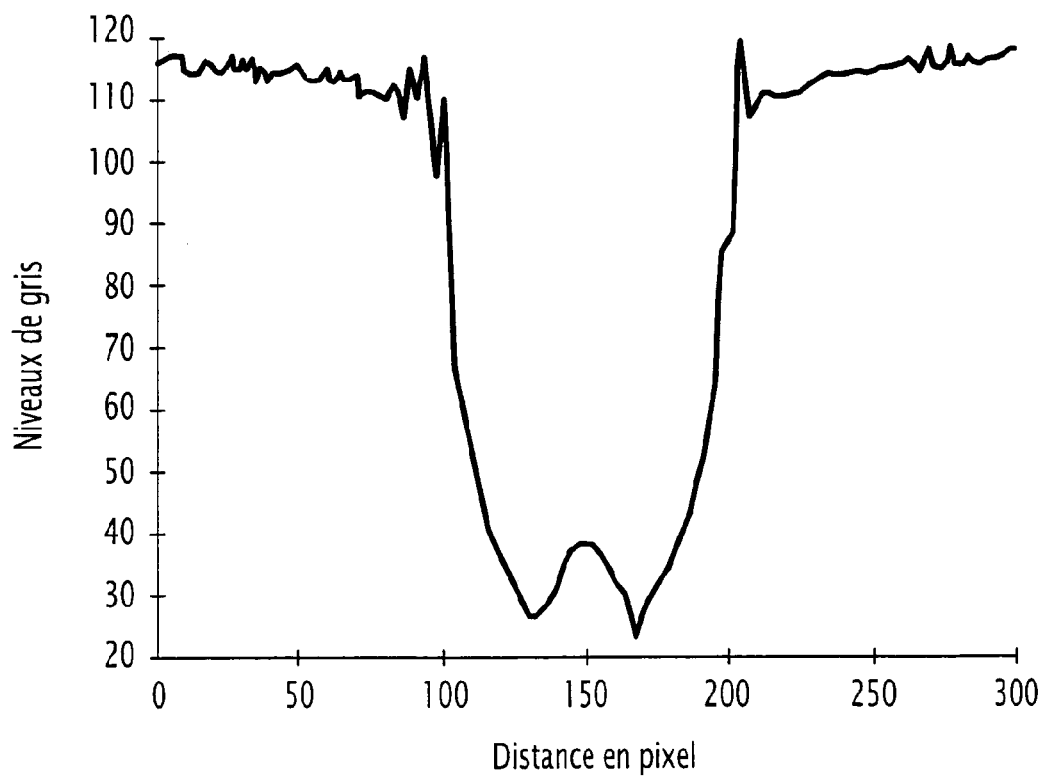
FIG. 4 is a graph illustrating the greyscales along a horizontal line L of FIG. 3.

FIG. 4 illustrates the profile along the line L, expressed in greyscales in the image of FIG. 3, for each pixel of the detector placed along the line L. The profile has variations in the greyscales inherent in the presence of the fibre, the wavelength, the nature, the density and the thickness of the fibre.

Figure 5:
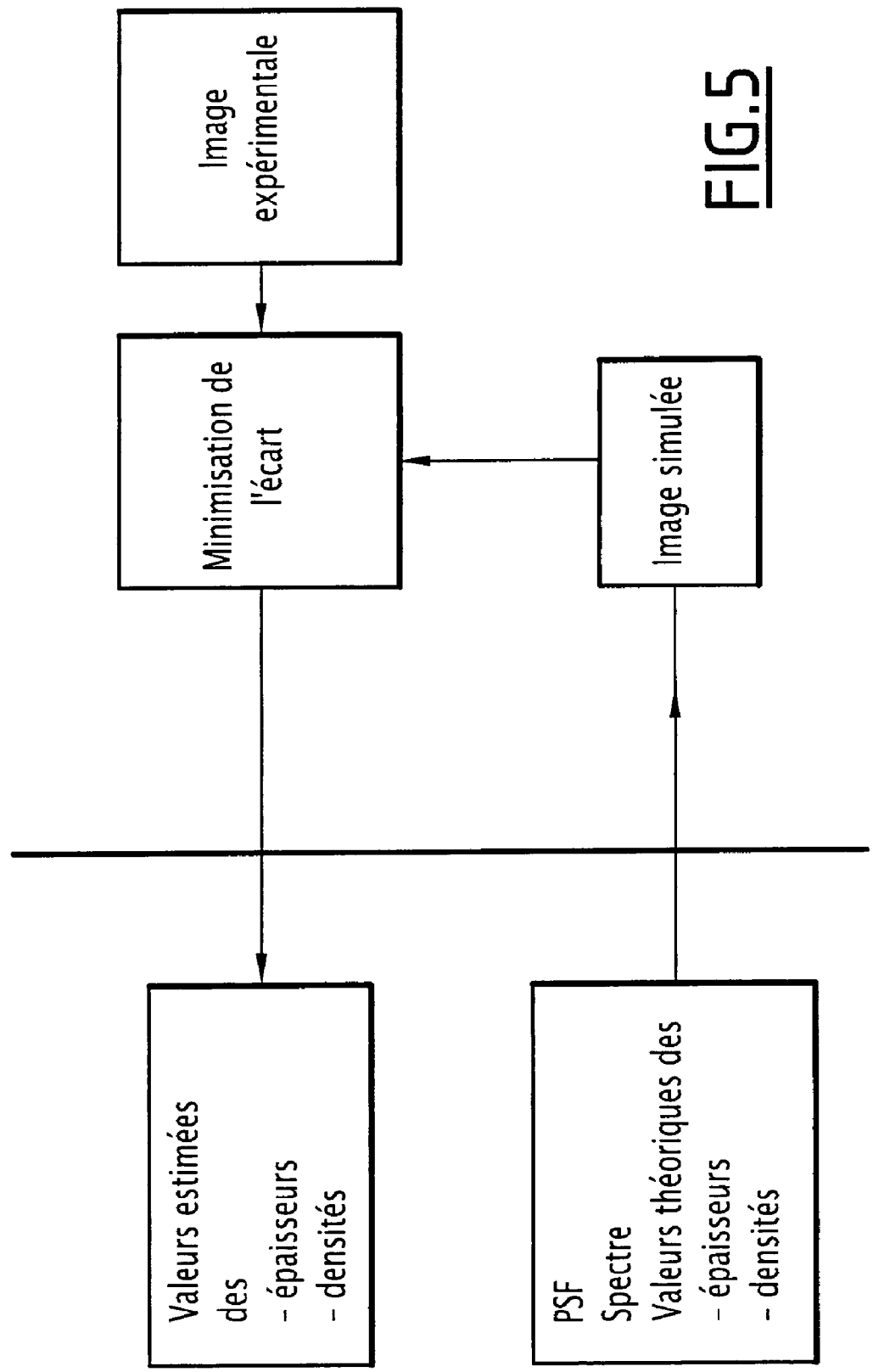
FIG. 5 is a schematic block diagram of the step for calculating the thicknesses and the densities of the various layers of the particle of FIG. 1, from the experiment image of this particle obtained with the installation of FIG. 2.

The data-processing unit 19 then calculates a simulated profile of the line L. As illustrated in FIG. 5, the unit 19 uses, to this end, input values for different parameters. These parameters are:
- the pulsed response of the detector 17 for each pixel along the line L;
- the characteristic spectrum of the source 13;
- the thickness and the density of the core 3 and each of the layers 5, 7, 9 and 11 of the particle 21.

Then, the unit 19 compares the simulated profile with the experiment profile and adjusts the densities and the thicknesses of the layers 5, 7, 9 and 11 in an iterative manner in order to minimise the difference between the experiment and simulated profiles. The iterative process is stopped when the difference is stabilised at a value close to zero, that is to say, when the iterative process has reached a point of convergence. The unit 19 provides as a result of the analysis the values of the densities and the thicknesses of the layers 5, 7, 9 and 11 corresponding to the simulated profile towards which the iterative process has converged.

The profile simulated by the unit 19 is calculated pixel by pixel along the line L. In the following description, a system of coordinates designated x, y, z will be used, z being the coordinate along an axis parallel with the propagation direction F of the radiation beam X, x and y being the coordinates in a plane parallel with the photosensitive zone of the CCD camera, the plane being perpendicular relative to the direction F.

To this end, the unit 19 uses the following general equation:

$$I_{simulée}(x,y) = I_{théorique}(x,y) * PSF(x,y)$$

In particular, and with some approximations, it is possible to use:

$$I_{simulée}(x, y) = \qquad (1)$$
$$I(x, y) = \left(P_d(x, y) * \left[\exp\left(-\frac{1}{2}\int \mu(z)\exp i\varphi(x, y, z)dz\right)\right]\right) * PSF(x, y)$$

where I(x, y) is the intensity of the radiation received by each pixel.

$P_d(x, y)$ is a term which characterises the propagation of the radiation between the particle and the detector, that is to say, the development of the wave front along the path from the particle to the detector. It is expressed by the following equation (2):

$$P_d(x, y) = \frac{1}{i\lambda d_2}\exp\left[i\frac{\pi}{\lambda d_2}(x^2 + y^2)\right] \qquad (2)$$

with
λ wavelength of the X-radiation;
$d_2$ distance between the particle 21 and the detector 17.

The second term of the equation (1) characterises the attenuation of an X-ray which extends through the particle 21. This expression is integrated along the entire path traveled by the radiation inside the particle 21. In this expression, μ represents the attenuation coefficient per unit length of the material through which the radiation passes.

The third term of the equation (1) characterises the phase shift to which the X-ray is subjected when passing through the particle 21. In this expression, φ is the X-ray phase. φ is expressed by the following equation (3):

$$\varphi(x, y) = \frac{2\pi}{\lambda}\int (1 - \delta(x, y, z))dz \qquad (3)$$

with:

$$\delta = \frac{r_C N_a \lambda^2 \rho}{2\pi}\sum q_j(Z_j + f'_j)/A_j \qquad (4)$$

where:
δ is the real portion of the refractive index of the material through which the X-ray passes,
$r_C$ is the classical electron radius,
$N_a$ is the Avogadro number,
ρ is the density of the material through which the radiation passes.

For each of the types j which constitute the material through which the radiation passes:
$q_j$ is the mass fraction of this element in the material,
$Z_j$ is the atomic number of the element,
$f'_j$ is the real portion of the dispersion correction of the atomic diffusion factor, and
$A_j$ is the atomic mass of the element.

In the equation (3), the integral is carried out over the entire length of the path of the X-ray through the particle 21.

PSF is the pulsed response of the detector for the corresponding pixel.

In the equation (1), the asterisks indicate convolution products.

In practice, in order to simplify the calculations, the unit 19 first calculates, for each pixel along the profile, the imaginary and real portions of the propagation term, the attenuation term and the phase shift term. It then calculates the Fourier transforms of these three terms and calculates, for each pixel, the product of the Fourier transforms of these three terms. It determines the inverse Fourier transform of the product obtained. Then, it calculates the square module of the amplitude of the result of the inverse Fourier transform. The energy of the simulated X-ray is thereby obtained with respect to each pixel of the detector. Finally, the simulated profile is determined by means of convolution of the energy obtained beforehand for each pixel via the PSF.

The determination of the values of thickness and density for the layers allowing the deviation to be minimised between the simulated profile and the experiment profile can be carried out using different algorithms which are known per se. For example, it is possible to use the method which is referred to as gradient descent. It is also possible to use other methods, such as stochastic methods or simulated annealing or genetic algorithms. Among these methods, it is possible to use the algorithm which is referred to as the stochastic gradient, local random search or advanced local random search algorithm.

These methods are known and therefore will not be described here in greater detail.

In order to increase the precision of the method, the pulsed response of the detector (PSF) is determined in accordance with the method which will be described below. This operation is carried out before carrying out the determination of the densities and the thicknesses of the layers of the particle. It must be repeated each time one of the parameters of the measurement installation is modified, that is to say, the distance d1 between the source 13 and the particle 21, the distance d2 between the particle 21 and the detector 17, the characteristics of the source and the characteristics of the detector. On the other hand, it is not necessary to redetermine the PSF for each particle characterised, on condition that the operating parameters of the installation are not changed.

The pulsed response of the detector is determined, for example, by:
acquiring on the detector an experiment image of a sample element of known geometry and density;
extracting a profile of the experiment image, for example, along the line L;
calculating a simulated profile of the sample element using the equation indicated above;

determining the pulsed response of the detector along the line L by minimising the deviation between the simulated profile and the experiment profile.

The sample element is placed against the detector 17, and not remotely like the particle 21. This sample element is typically a plate of split silicon. It is placed in such a manner that the line L intersects an outer edge of the plate.

The pulsed response of the detector along the line L can be expressed in the following manner:

$$PSF(x) = \left[2\exp\frac{-x^2}{e_{PSF}^2}(\sqrt{\pi}\cdot e_{PSF}\cdot f_{PSF})^{-1} + \left(\left(1+\frac{x^2}{b_{PSF}^2}\right)\cdot b_{PSF}\cdot c_{PSF}\right)^{-1}\right]$$

$b_{PSF}$, $c_{PSF}$, $e_{PSF}$, $f_{PSF}$ are parameters whose values are determined by minimising the deviation between the simulated profile and the experiment profile of the sample element. This determination is carried out, as set out above, using conventional iterative algorithms such as gradient descent or stochastic algorithms, such as the stochastic gradient, local random search or advanced local random search algorithm.

In order to further increase the precision of the method, it is possible to acquire on the detector two successive images of the particle 21. The second image is produced after having caused the particle 21 to pivot through approximately 90° about a vertical axis in FIG. 2, that is to say, both perpendicular relative to the direction F and perpendicular relative to the line L.

The unit 19 determines, from the second image, the thickness of the material through which the X-rays pass in the first position of the particle 21. The determination of the densities of the layers is carried out using the first experiment image, taking into account the material thickness values determined from the second image. This is particularly advantageous for particles to be characterised which are not completely spherical.

The method allows the thicknesses and the densities to be determined for the layers surrounding the fissile material core of the particle in a very precise manner. In particular, as illustrated in the table below, it allows the densities of the layers to be determined with an error of less than 6%.

Comparative tests have been carried out on particles of several types. The density of at least one of the layers of each particle has been determined using the method of flotation and/or using the method of phase contrast X radiography described above. In this last method, in order to carry out the minimisation between the experiment and simulated profiles, an algorithm of the advanced local random search type has been used. Furthermore, the pulsed response of the detector has been determined for each particle from the experiment image of the particle in accordance with the method described below.

| Number of layers | Type of layers | Density by flotation | Density by X radiography | Difference (%) |
|---|---|---|---|---|
| 1 | Buffer layer | 0.97 | 1.02 | 5.15 |
| 2 | Pyrocarbon | 1.89 | 1.96 | 3.70 |
| 3 | SiC | 3.202 | — | — |
| 4 | Pyrocarbon | 2.03 | 1.92 | 5.42 |
|   | SiC | — | 3.30 | — |
|   | Pyrocarbon | — | 1.86 | — |

According to a second aspect of the invention, which is independent from the first, the experiment image of the particle acquired by the detector is used to determine the presence of structural anomalies inside the layers 5, 7, 9 and 11 of the particle, or between the layers of the particle. The structural anomalies which it is thus possible to detect are, inter alia, the following:

occurrences of loss of cohesion between layers, that is to say, the zones where two superimposed layers are not in contact with each other but instead where there is a space between the two layers;

the cracks or the cavities which are located within the same layer;

the zones inside a layer where it has abnormal porosity;

the zones where a layer has a thickness defect.

These various structural anomalies, with the exception of the thickness defect, create characteristic interference fringes on the experiment image, which it is possible to identify visually and associate with a type of structural anomaly.

The method described above has a number of advantages. It is based on the analysis of an experiment image of the element to be characterised so that it is non-destructive and does not involve products which are harmful to the environment. It is rapid since the estimation of the thicknesses and the densities of the layers of the particle can be carried out in less than two hours.

Owing to this rapidity, this method is capable of being used to carry out the characterisation of a significant number of particles of nuclear fuel of the batch which is intended to form a core of a high-temperature nuclear reactor.

No specific preparation of the particles to be characterised is required to implement the method.

The method can be used to determine the thicknesses and the densities of all the layers which surround the fissile material core of the particle.

The method is precise, and allows the thicknesses and the densities to be determined with an error of less than 6%. The step for determining the pulsed response of the detector described above contributes significantly to the precision of the method.

The method described above may have a number of variants.

It may be used for all types of element which have superimposed layers. These elements may have any type of shape, different from the spherical shape set out above. These shapes may be regular or irregular. The layers may be constituted by all kinds of different material, the method not being limited to the materials set out above.

The method may in particular be used to characterise the fuel particles of all types of high-temperature reactor, for example, of the type known by the acronyms HTR (High Temperature Reactor), HTTR (High Temperature Engineering Test Reactor), VHTR (Very High Temperature Reactor), HTGR (High Temperature Gas-Cooled Reactor), THTR (Thorium High Temperature Reactor), GT-MHR (Gas Turbine Modular Helium Reactor), MHTGR (Modular High Temperature Gas Reactor) and PBMR (Pebble Bed Modular Reactor).

The use of an intermittent source 13 allows the precision of the results to be increased. However, it is possible to use other types of source which generate, for example, stable waves. The source may also not be monochromatic, but instead polychromatic.

In the example described above, the physical characteristics of the layers are determined by minimising the deviation between a portion of the image, in this instance a profile which is taken along a line, and a simulated profile. More generally, it is possible to extract from the experiment image and to carry out the deviation minimising operation not on a profile which is taken along a line, but instead over all kinds of zones of the experiment image. In this manner, it is possible to extract a plurality of mutually parallel or non-parallel lines. It is also possible to extract one or more two-dimensional zones of the screen. It is also possible to carry out the minimisation of the deviation taking into consideration the whole of the experiment image. Of course, as the number of pixels considered in the zone selected increases, the result becomes more precise, but the calculation time becomes longer.

The pulsed response of the detector used to calculate the simulated image can be determined in different manners. It can be determined as described above, by minimising the deviation between the simulated and experiment images of a plate placed against the detector. It may also be determined in a similar manner using a plate which is placed at a distance d2 from the detector. It is also possible to use a predetermined value, which is not re-evaluated when the operational parameters of the characterisation device are modified. It is also possible to carry out the determination of the PSF for each particle characterised, from the experiment image of this particle. This operation is carried out before the determination of the densities and thicknesses of the different layers of the particle to be characterised. It involves determining the parameters $b_{PSF}$, $c_{PSF}$, $e_{PSF}$ and $f_{PSF}$ which minimise the deviation between the experiment image of the particle and a simulated image of the particle. The simulated image is calculated using the equations set out above, taking into account the theoretical values of thickness and density of the layers of the particle.

The invention claimed is:

1. A method for characterization of an element (1, 21), the element being a substantially spherical particle which comprises a plurality of layers (5, 7, 9, 11) which are substantially spherical, substantially concentric and superimposed, said superimposed layers (5, 7, 9, 11) being separated from each other by means of substantially spherical interfaces, wherein the method comprises at least the following steps:
   illuminating the entire element (1, 21) with radiation (15) emitted from an x-ray source (13), in such a way that some x-rays are transmitted through all the superimposed layers successively;
   acquiring on a detector (17) radiation (23) transmitted through the element (1, 21), this transmitted radiation forming on the detector (17) an experiment image of the element (1, 21), said experiment image being obtained by absorption of incident x-rays through the element, said experiment image being formed substantially by x-rays transmitted directly through the element, including the x-rays transmitted through all the superimposed layers, and showing the interfaces between the layers of the element, the detector (17) being placed at such a distance from the element (1, 21) such that diffraction interference fringes appear superimposed on the experiment image at the interfaces between the layers (5, 7, 9, 11);
   determining an approximate value of at least one physical characteristic of at least one specific layer (5, 7, 9, 11) by means of calculation from the experiment image, the determination step being carried out by minimizing the deviation between the experiment image and a simulated image of at least a portion of the experiment image of the element (1, 21).

2. The method according to claim 1, wherein the detector (17) is a charge transfer camera for direct or indirect detection.

3. The method according to claim 1, wherein the physical characteristic to be determined is the density.

4. The method according to claim 1, wherein the physical characteristic to be determined is the thickness.

5. The method according to claim 1, wherein it comprises a prior step for determining the pulsed response of the detector (17), carried out by:
   acquiring on the detector (17) an experiment image of a sample element;
   calculating a simulated image of at least a portion of the experiment image of the sample element;
   determining the pulsed response of the detector by minimizing the deviation between the simulated image and the experiment image of the sample element.

6. The method according to claim 5, wherein the sample element is placed against the detector (17), the simulated image being carried out for at least one edge of the sample element.

7. The method according to claim 1, wherein the experiment image is substantially circular, the simulated image being a profile taken along a line (L) which extends through a diameter of the experiment image.

8. The method according to claim 1, wherein the particle (1, 21) is a particle of nuclear fuel.

9. The method according to claim 1, wherein the experiment image is substantially circular.

10. The method according to claim 1, wherein the detector is located along a substantially straight line passing by the x-ray source and the particle, opposite the x-ray source with respect to the particle.

* * * * *